United States Patent [19]
Fuchs

[11] Patent Number: 5,773,681
[45] Date of Patent: Jun. 30, 1998

[54] METHOD OF PRODUCING ELECTROLYTE-ENRICHED PLANT EMBRYOS

[76] Inventor: Norbert Fuchs, A-5571, Mariapfarr No. 135, Austria

[21] Appl. No.: 567,208

[22] Filed: Nov. 29, 1995

[51] Int. Cl.$^6$ ............................... A01C 1/00; A01H 3/04
[52] U.S. Cl. ............................... 800/200; 47/57.6; 47/58; 47/DIG. 9; 800/DIG. 11; 800/DIG. 14; 800/DIG. 15; 800/DIG. 18; 800/DIG. 21; 800/DIG. 23; 800/DIG. 24; 800/DIG. 26; 800/DIG. 55; 800/DIG. 56; 800/DIG. 57; 800/DIG. 58
[58] Field of Search ............................. 47/58, 14, DIG. 9; 800/200, DIG. 55, DIG. 56, DIG. 57, DIG. 58, DIG. 11, DIG. 14, DIG. 15, DIG. 18, DIG. 21, DIG. 23, DIG. 24, DIG. 26

[56] References Cited

U.S. PATENT DOCUMENTS

| 2,051,460 | 8/1936 | Von Skrbensky | 47/58 |
| 4,130,964 | 12/1978 | Caballero | 47/16 |
| 4,618,454 | 10/1986 | Ballard et al. | 252/500 |

FOREIGN PATENT DOCUMENTS

| 396 414 | 1/1993 | Austria | A01C 1/00 |
| 41 22 133 | 1/1993 | Germany | A01G 7/04 |
| 2 100 112 | 12/1982 | United Kingdom | A01C 1/00 |

OTHER PUBLICATIONS

Harmuth–Hoene, "Dietary Fiber and the Bioavailability of Essential Trace Elements, a Controversial Topic," *Trace Element–Analytical Chemistry in Medicine and Biology*, 4:107–120, 1987.

Harmuth–Hoene et al., "The Influence of Germination on the Nutritional Value of Wheat, Mung Beans and Chickpeas," *Z Lebensm Unters Forsch*, 185:386–393, 1987.

Harmuth–Hoene, A.E. and Meuser, F., "Zwitschrift fuer Ernaehrungswissenschaft", *Z Ernaehrungswiss*, 26(4):250–267, 1987.

Meier–Ploeger, "The Importance of Sprouts and Seeds Sprouts in Whole–Food Nutrition," *Nutrition*, 14:317–323, 1990.

Search Report of the Austrian Patent Office.

*Primary Examiner*—Douglas W. Robinson
*Assistant Examiner*—Melissa L. Kimball
*Attorney, Agent, or Firm*—Arnold, White & Durkee

[57] ABSTRACT

The invention relates to plant embryos having an increased electrolyte content as compared to embryos germinated in tap water, as well as to a method of producing these plant embryos, wherein germinative seeds are germinated in an electrolyte solution.

13 Claims, 8 Drawing Sheets

Chromatograms of a standard solution (104 μg/g thiamin hydrochloride) and the sample B0S6 (Fenugreek embryos after 3 days of germination)

METHOD OF PRODUCING ELECTROLYTE-ENRICHED PLANT EMBRYOS

The invention relates to plant embryos as well as to a method of producing the same.

The present food supply as well as the consumption behavior is characterized by foodstuffs having a high content of calories while simultaneously having a low portion of dietary fibre and a low nutrient density (a low content of vitamins, bulk elements, trace elements, bioactive plant substances etc.). Thus, the foodstuffs preferably consumed, such as fine flour products (bread, baked goods, egg pasta, confectioneries), sugar and sugar-containing foodstuffs (sweets, sugar-containing lemonades), fast food, and foodstuffs having a high content of animal proteins, only insufficiently cover the demand for dietary fibres, and in particular, for vitamins, bulk elements and trace elements. The consequence of this consumption behavior is a continuously increasing percentage of nutritionally caused and nutritionally dependent diseases, such as overweight, chronic defaecation problems, hypertension with elevated blood lipid and triglyceride concentrations, dysglycemia, hepatic and bilious affections, circulatory disturbances, diseases of the digestive organs, caries, rheumatic diseases, gout, skin diseases, allergies and disturbances of the immune defence system.

In parallel to the devitaminization and demineralization of frequently consumed staples (e.g. caused by the refining of the various cereal flours and vegetable oils), statistically there is a continuously increasing contamination of the staples with foreign and harmful substances (organohalogen compounds, agrochemicals, such as pesticides, growth regulating agents, germination inhibiting agents and fertilizers, heavy metals, medicament residues, phytotoxins etc.).

Last but not least, for reasons of production technology, the basic substances of foodstuffs are admixed with colorants, preservatives, antioxidants, emulsifiers, stabilizing agents, thickeners, gelating agents, modifying starches, acidifying agents, acid regulators, separating agents, coating agents, dip-coating masses, enhancers, flavors, sugar substitutes, artificial sweeteners and other technological substances.

To counteract this deterioration of the nutritional situation or these negative developments of the nutritional behavior, more and more consumers are interested in changing these nutritional habits and to increasingly consume natural foodstuffs which enable a sufficient supply with dietary fibres, mineral and trace elements, vitamins, vegetable proteins etc. (so-called "whole-food nutrition").

Whole-food nutrition mainly consists of ecologically produced vegetable foodstuffs, isolated or refined products being avoided as far as possible.

Plant embryos meet the principles of high-value nutrition, both in terms of nutrition physiology and in terms of ecology. Compared to ungerminated seeds, the plant embryo has a better quality of protein, a higher content of polyunsaturated fatty acids, an improved bioavailability of essential minerals, and a higher vitamin and dietary fibre content. Moreover, a plurality of negatively valued components in the seed, such as trypsin inhibitors, hemagglutinins, saponins, flatulent substances etc., decrease with an increasing duration of germination.

Thus, plant embryos constitute a valuable enrichment of the food, particularly since they are inexpensive as compared to vegetable varieties, they are always fresh, independent of seasons, rich in dietary fibres, rich in vitamins and minerals, and in addition tasty and wholesome.

In general, the plant growing from a grain of seed is called a plant embryo for the first few days of germination. Prior to germination, the pre-formed plant embryo in the seed is in a state of rest in which all metabolic processes are reduced to a minimum, and there is no growth. The swelling process starts with the uptake of water into the seed, thereby causing the activity of the metabolic processes. The seed shell, which until then has been impermeable to oxygen, becomes respiratorily active, phytohormones (in particular gibberellic acid) are synthesized within the plant embryo, and these in turn stimulate the synthesis of specifically active enzymes. These enzymes degrade the reserve substances stored in the seed in amounts specific of the respective type (Meier-Ploeger "Die Bedeutung von Sprossen und Keimen in der Vollwerternahrung", Ernahrung/Nutrition (6) (1990), 317–323).

Numerous studies have been carried out on the changes of the content of the components of the plant embryo as compared to the seed, these studies often being contradictory. It is not clear to what extent these discrepancies are due to differences in the nature of the starting material, the conditions of germination or the method of determining the nutritional value (Harmuth-Hoene et al., "Der Einfluβ der Keimung auf den Nährwert von Weizen, Mungbohnen und Kichererbsen", Z. Lebensm. Unters. Forsch., 185 (1987), 386–393).

Also the data on the changes of the mineral content of plant embryos are contradictory. There seems to be agreement on the fact that, depending on the solubility of the minerals, very different losses of minerals may occur during germination. Thus, various authors have observed a decrease of iron in an amount of from 9 to 21%, of potassium in an amount of 27%, and of copper in an amount of between 12 and 17% (Hartmuth-Hoene (1987)).

Furthermore, also high losses of calcium and magnesium have been reported in the course of germination.

The present invention thus has as its object to provide plant embryos improved in terms of nutrition physiology relative to conventional plant embryos.

According to the invention, this object is achieved by plant embryos having a higher electrolyte content as compared to germination in tap water.

The plant embryos according to the invention have a content increased by at least 10 to 20%, preferably by at least the 1.5 to 3-fold, in particular by at least the 5 to 10-fold, of one or several electrolytes, preferably of zinc, iron, potassium, magnesium, copper, manganese, strontium, selenium, molybdenum, chromium, arsenic, vanadium and/or cobalt ions, as compared to conventionally germinated seeds.

Hitherto, conventional seed germination in which the seeds were germinated in distilled water or in tap water, always involved partly considerable losses of these nutritionally important components. As the tests accompanying the present invention revealed, these losses were caused both by the starting metabolic process of the plant embryo itself, and by the nature of the swelling agent water which contributed to an additional electrolyte leach-out of the plant embryo, since in contrast to the at-rest state (seed), the shell of the plant embryo is very well susceptive to electrolyte leach-out.

Furthermore, it has been shown that the electrolyte-enriched plant embryos according to the invention do not only exhibit a higher concentration of minerals, but, on account of the increased mineral content, are also generally improved in terms of their components, e.g. they have a higher vitamin content.

A preferred production method of the plant embryos according to the invention consists in that germinative seeds are introduced into an electrolyte solution, and the plant embryos are incubated in this electrolyte solution at a suitable temperature for a period of time sufficient to achieve electrolyte enrichment in the plant embryos.

It was surprising that by using an electrolyte solution, i.e. a solution having an increased ion concentration, in contrast to conventional germination solutions (tap water or distilled or sterilized water), the electrolyte losses occurring in the course of germination could be compensated or even reversed by an electrolyte flow from the germination solution into the plant embryos, whereby plant embryos formed which partly even had an increased content of electrolytes as compared to the seed.

By electrolyte solution there is further meant an aqueous solution admixed or enriched with one or several electrolytes, as defined below.

With the production method according to the invention, the ion concentration of the electrolyte solution is to be higher by at least 10 to 20% than that of conventional tap water, preferably the ion concentration of the electrolyte solution at least in terms of iron and/or copper and/or manganese and/or strontium and/or lithium and/or molybdenum ions is twice as high as that of conventional tap water, particularly preferably at least five times as high, in particular at least ten times as high.

The temperature suitable for carrying out the germination is, of course, different for each type of seed. In principle, the germination temperature described in the prior art for the respective type of seed is also to be applied for the method according to the invention. Preferably, this temperature ranges between 10° and 50° C., in particular between 20° and 30° C.

The time required to achieve a sufficient electrolyte enrichment in the plant embryos is also different for each type of embryo, it also depends on which electrolyte values are to be attained in the embryo. Here, too, the germination periods described in the prior art for a certain type are to be taken as standard values, preferably thus germination is carried out during a period of approximately 12 to 120 hours, in particular approximately 60 to 100 hours.

It goes without saying that both the germination temperature and the germination period can be optimised for each system by a skilled artisan without problems by simple tests, and for certain types they may very well lie above or below the standard values indicated above.

According to the invention, the preferred plant embryos are the embryos of common vegetable foodstuffs, in particular the embryos of leguminosae and cereal seeds. Thus, particularly preferred are the embryos of wheat, buckwheat, quinoa, mung bean, fenugreek, radish, alfalfa, maize, squash, rye, barley, rice, adzuki-beans, peas, millet, chick pea, cress, linseed, lentil, mustard, sesamum, soybean, sunflower and amaranth.

According to a preferred embodiment, the electrolyte solution used in the method according to the invention contains 1 mg/l or more, preferably 10 mg/l or more, in particular 50 mg/l or more, zinc and/or iron and/or potassium and/or magnesium ions, 0.5 mg/l or more, preferably 5 mg/l or more, in particular 25 mg/l or more, copper and/or manganese and/or strontium and/or lithium ions, 0.1 mg/l or more, preferably 1 mg/l or more, in particular 5 mg/l or more, selenium and/or molybdenum and/or chromium and/or arsenic and/or vanadium and/or cobalt ions, with the proviso that the ion concentration of the electrolyte solution differs in at least one ion species from the ion concentration of tap water by at least 10 to 20%.

A particularly preferred electrolyte solution contains at least 0.5 mg/l copper and/or 1 mg/l zinc and/or 0.1 mg/l cobalt ions and preferably at least 0.1 mg/l molybdenum and/or 0.5 mg/l lithium and/or 1 mg/l selenium and/or 1 mg/l vanadium ions.

After their production, depending on their intended purpose, the electrolyte-enriched plant embryos according to the invention may be washed, dried, and possibly further processed in a manner suitable for sale thereof. Particularly preferred is the processing of the plant embryos according to the invention to fresh food, sandwich spreads, to bakery goods or to snack-type food or food supplements in the form of mueslis, chewing tablets, capsules or liquids.

Another aspect of the present invention is the treatment and prevention of nutritionally caused or nutritionally dependent diseases in humans and animals, such as overweight, chronic defaecation problems, hypertension with elevated blood lipid and triglyceride concentrations, dysglycemia, hepathic and bilious affections, circulatory disturbances, diseases of the digestive organs, caries, rheumatic diseases, gout, skin diseases, allergies and disturbances of the immune defence system, devitaminization or demineralization syndromes, which treatment or prevention comprises the administration of plant embryos produced according to the present invention or processed products derived from such plant embryos. The amount to be administered is highly dependent on the disease (or the stage of the disease) to be treated or prevented, it should, of course, be sufficient to achieve a suitable effectiveness.

The invention will be explained in more detail by way of the following examples and the associated drawings, to which, however, it shall not be restricted.

FIG. 1 shows the enrichment of trace elements during germination of wheat;

FIG. 2 shows the enrichment of trace elements during germination of buckwheat,

FIG. 3 shows the enrichment of trace elements during germination of quinoa; and

FIG. 4 shows the chromatographic vitamin B1 determination in a standard solution with 104 μg/g thiamine hydrochloride and in the sample BoS6 (fenugreek embryos after 3 days of germination).

EXAMPLES

1. Enrichment of Trace Elements During Germination of Wheat, Buckwheat and Quinoa 1.1. Germination Germinative seeds of wheat (*Triticum aestivum*), buckwheat (*Fogpyrum esculentum*) and quinoa (*Chenopodium quinoa*) were used for the germination experiments. Approximately 90 g of the three different cereal seeds were each germinated with five different solutions: (1) double-distilled water, (2) tap water, (3) electrolyte solution 1, (4) electrolyte solution 2 and (5) electrolyte solution 3 (cf. Table 1). To produce the electrolyte solutions, only p.a. chemicals and double-distilled water were used.

TABLE 1

Trace element concentrations of the electrolyte solutions used

| Substance | Electrolyte solutions c [mg/l] | | | Element | Electrolyte solutions c [mg/l] | | |
|---|---|---|---|---|---|---|---|
| | 1 | 2 | 3 | | 1 | 2 | 3 |
| Zinc sulfate × 7H$_2$O | 4.40 | 44.0 | 220 | Zn | 1.0 | 10 | 50 |
| Ammonium ferric sulfate | 8,95 | 89,5 | 447 | Fe | 1.0 | 10 | 50 |
| Manganese chloride | 1.48 | 14.8 | 74 | Mn | 0.5 | 5 | 25 |
| Copper gluconate | 3.57 | 35.7 | 178 | Cu | 0.5 | 5 | 25 |
| Sodium selenate | 0.24 | 2.4 | 12 | Se | 0.1 | 1 | 5 |
| Sodium molybdate | 0.25 | 2.5 | 12.5 | Mo | 0.1 | 1 | 5 |
| Chromic chloride | 0.51 | 5.1 | 25.5 | Cr | 0.1 | 1 | 5 |
| Strontium lactate | 1.69 | 16.9 | 84.5 | Sr | 0.5 | 5 | 25 |
| Lithium carbonate | 2.68 | 26.8 | 134 | Li | 0.5 | 5 | 25 |
| Disodium arsenate | 0.56 | 5.6 | 28 | As | 0.1 | 1 | 5 |
| Ammonovanadate | 0.23 | 2.3 | 11.5 | V | 0.1 | 1 | 5 |
| Cobalt chloride × 6H$_2$O | 0.40 | 4.0 | 20 | Co | 0.1 | 1 | 5 |

Prior to the germination phase as such, the wheat seed was soaked in the respective solutions for 12 hours and the quinoa seed for 8 hours. The buckwheat seed was used without previous soaking.

Germination took place at room temperature (19° to 21° C.) and normal day-night light ratios in commercial germinators consisting of transparent, superimposed plastics dishes with drainage means. The total germination period (soaking time+germination time) was 96 hours for wheat and quinoa, 72 hours for buckwheat. During germination, the plant embryos were flushed twice daily with the respective solutions (250 ml/90 g). After the harvest, all the plant embryos were thoroughly flushed with double-distilled water (3×with ca. 800 ml) and aliquoted. One portion of the sample was immediately filled into little plastic bags and deep-frozen at −18° C. The other portion of the sample was flushed again at 70° C. with hot tap water before freezing (3×with ca. 800 ml) (cf. Table 2).

TABLE 2

List of Samples

| | Wheat | Buckwheat | Quinoa |
|---|---|---|---|
| Seed | WS0 | BS0 | QS0 |
| Germination with distilled water | WS1 | BS1 | QS1 |
| Plant embryos washed hot | WS1H | BS1H | QS1H |
| Germination with tap water | WS2 | BS2 | QS2 |
| Plant embryos washed hot | WS2H | BS2H | QS2H |
| Germination with electrolyte solution 1 | WS3 | BS3 | QS0 |
| Plant embryos washed hot | WS3H | BS3H | QS3H |
| Germination with electrolyte solution 2 | WS4 | BS4 | QS4 |
| Plant embryos washed hot | WS4H | BS4H | QS4H |
| Germination with electrolyte solution 3 | WS5 | BS5 | QS5 |
| Plant embryos washed hot | WS5H | BS5H | QS5H |

1.2 Preparing the Samples

The samples were dried in a freeze-drying installation (CHRIST ALFA 1-4 with installation control LDC-1M) as follows: The plant embryos (50 g each) were first deep-frozen at −30° C. (top-opening freezer) and subsequently at −45° C. (condenser space of the freeze-drying installation). This was followed by the main drying at −15° C. and at a pressure of 0.31 mbar (safety pressure 5 mbar). After 36 h the drying temperature (temperature of the sample dish of the installation) was raised to 0° C. After a total time of 72 h, the samples were completely dry and could be used to be further prepared. During the complete drying process it was made sure that the samples were never thawed. The dry plant embryos subsequently were homogenized in a contamination-free analysis mill (Retsch ZM 1000, with titanium rotor and titanium sieve; grain size 0.25 mm).

1.3. Determination of the Trace Element Concentrations with ICP-MS and GFAAS

Mineralization

Samples weighing approximately 200 mg were exactly weighed into a teflon vessel, admixed with 3 ml double distilled HNO$_3$, and 0.5 ml H$_2$O and mineralized in the microwave disintegration apparatus (MLS, 1200 mega, equipped with a rotor for 10 samples) with the following energy program: 2 min 250 W, 0.5 min 0 W, 10 min 250 W, 0.5 min 0 W, 5 min 450 W, 0.5 min 0 W, 7 min 600 W, 1 min 500 W. After cooling, the disintegration solutions were transferred to measurement flasks (10 ml) and filled up with H$_2$O nanopur. Two disintegrations were made of each sample. Each disintegration solution was measured three times, the measured concentrations being corrected with the concentrations of a disintegration blank. In parallel to the samples, two standard reference materials having a similar matrix composition (SRM-NIST 1575 Pine Needles and SRM-BCR 62 Olive Leaves) were analyzed to check the correctness of the analysis.

Measurement with GFAAS

The selenium and arsenic concentrations were determined by means of a Hitachi Z9000 GFAAS. The experimental conditions are summarized in Table 3. Quantitation was effected by means of external calibration curves.

TABLE 3

Experimental parameters for Determining the Se and As Concentrations with GFAAS

| | Se | As | | Se/As |
|---|---|---|---|---|
| Lamp current | 12 mA | 12 mA | Standard 1 | 0 µg/l |
| Wavelength | 195 nm | 196 | Standard 2 | 20 µg/l |
| Slit | 1.2 nm | 1.3 nm | Standard 3 | 50 µg/l |
| Cuvette | tube | tube | Standard 4 | 100 µg/l |
| Modifier | 2% Ni(NO$_3$)$_2$ | 2% Ni(NO$_3$)$_2$ | Standard 5 | 200 µg/l |
| Volume | 20 µl | 20 µl | | |

TABLE 3-continued

Experimental parameters for Determining the Se
and As Concentrations with GFAAS

Temperature Program

| | Se | | | As | | |
|---|---|---|---|---|---|---|
| Dry | 80° C. | 120° C. | 30 s | 80° C. | 120° C. | 30 s |
| Dry | 120° C. | 400° C. | 10 s | 120° C. | 500° C. | 20 s |
| Ash | 700° C. | 700° C. | 30 s | 800° C. | 800° C. | 30 s |
| Atom | 2400° C. | 2400° C. | 10 s | 2000° C. | 2000° C. | 10 s |
| Clean | 3000° C. | 3000° C. | 5 s | 3000° C. | 3000° C. | 5 s |
| Carrier gas | | 200 ml/min | | | 200 ml/min | |
| Interrupted gas | | 30 ml/min | | | 30 ml/min | |

Measurement with ICP-MS

Measurement of the concentrations of the trace elements Cr, Cu, Ni, Pb, Sr, Li, Fe, Zn, Mn, Cd, Co, Mo and V was carried out with an ICP-MS of Fisons, type: PlasmaQuad II+. The experimental parameters are summarized in Table 4. Before the measurement, the disintegration solutions were diluted 1:5 with $H_2O$. To correct internal equipment fluctuations, 50 ppb indium, 50 ppb gallium and 50 ppb rhenium were added to the disintegration solutions and to the standard solutions as an internal standard. Quantitation was effected by means of external calibration curves.

TABLE 4

Experimental Parameters for Determining the
Trace Element Concentrations with ICP-MS
ICP-MS plasmaQuad II+

| rf Power | 1.3 kW | Time/Sweep | 1.22 s |
|---|---|---|---|
| Colling-gas | 13.5 l/min | Dwell time | pulse count mode 320 $\mu$s |
| Auxiliary gas | 1.1 l/min | Data acquisition | peak jump mode |
| Nebulizer gas | 0.88 l/min | Uptake time | 60 s |
| Nebulizer | Meinhard Tr-30-A3 | Measuring time | 3 × 60 s |
| Spray chamber | double pass Scott type (−2° C.) | Wash time | 60 s |
| Sampling cone | Nickel, orifice 1.00 mm | | |
| Skimmer cone | Nickel, orifice 0.75 mm | Standard 1 | blank |
| Vacuum: expansion | 1.6 mbar | Standard 2 | 5 $\mu$g/l |
| Vacuum: intermediate | 1.0 × 10$^{-4}$ mbar | Standard 3 | 10 $\mu$g/l |
| Vacuum: analyzer | 2.1 × 10$^{-6}$ mbar | Standard 4 | 50 $\mu$g/l |

Figure 1A:
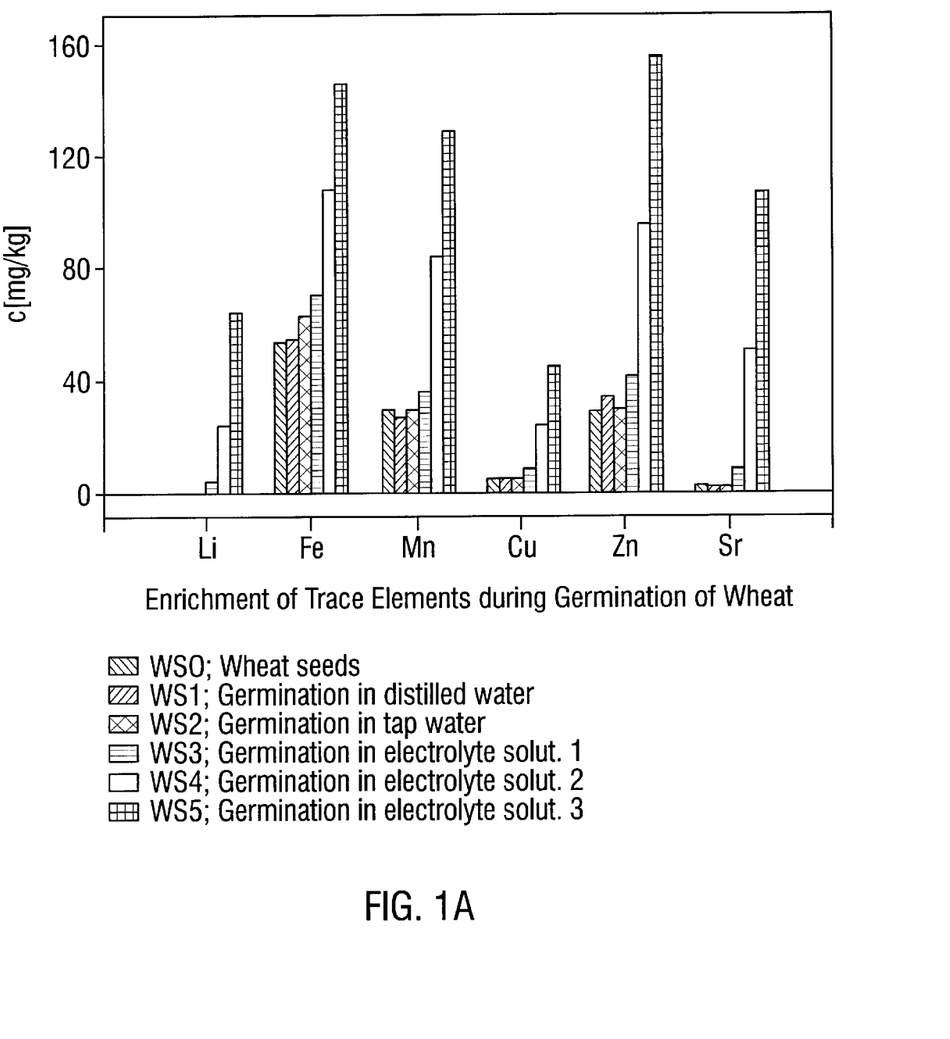
Figure 1B:
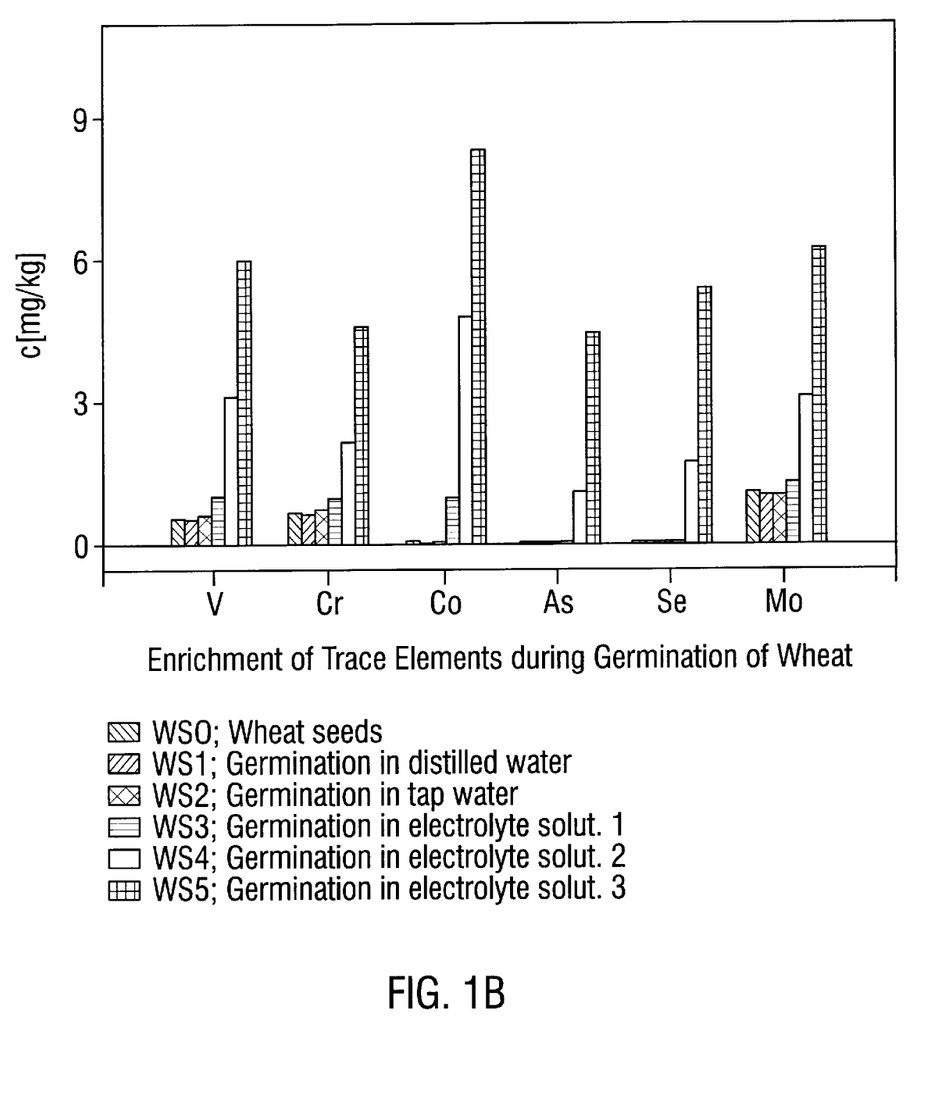
Figure 2A:
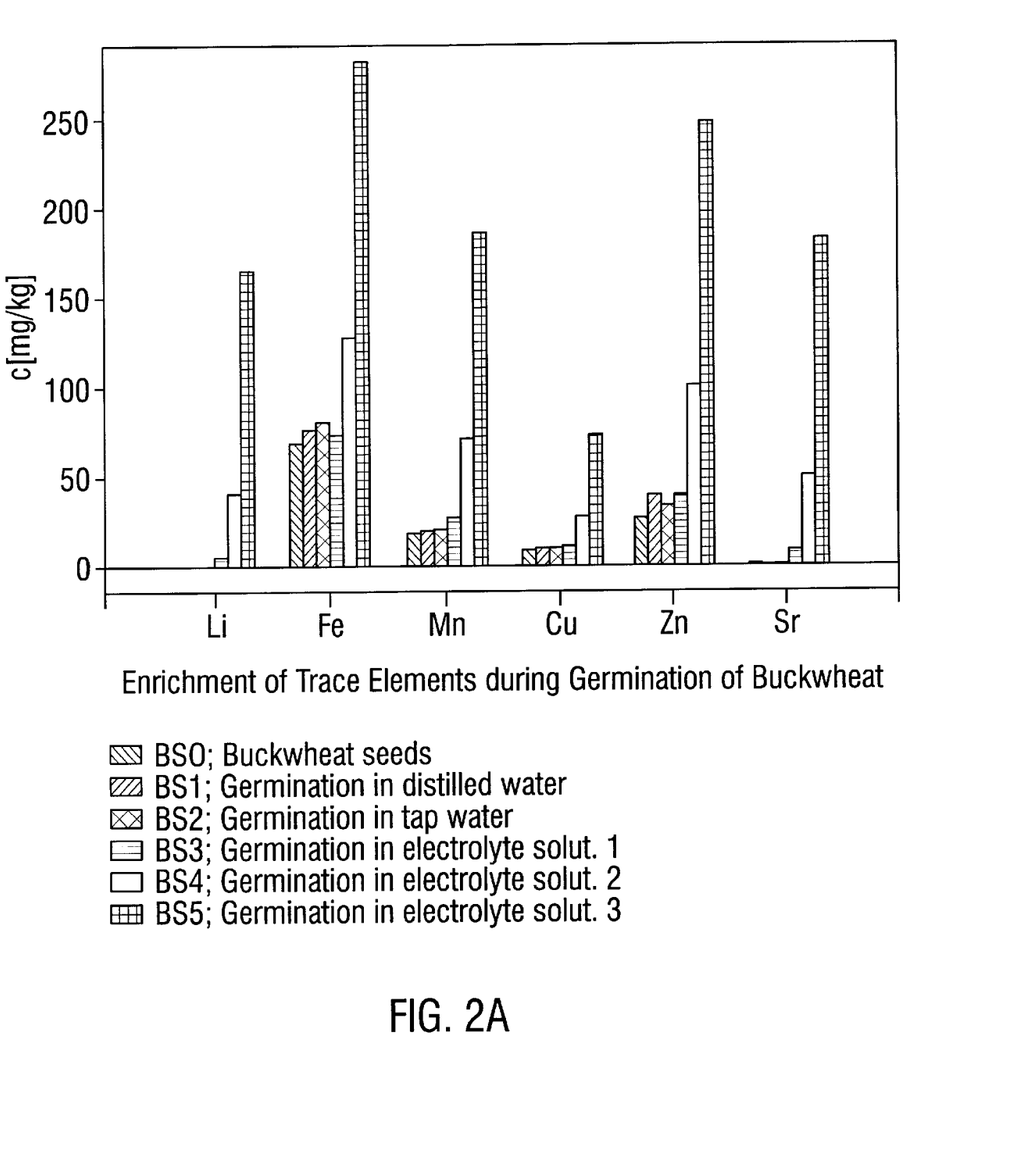
Figure 2B:
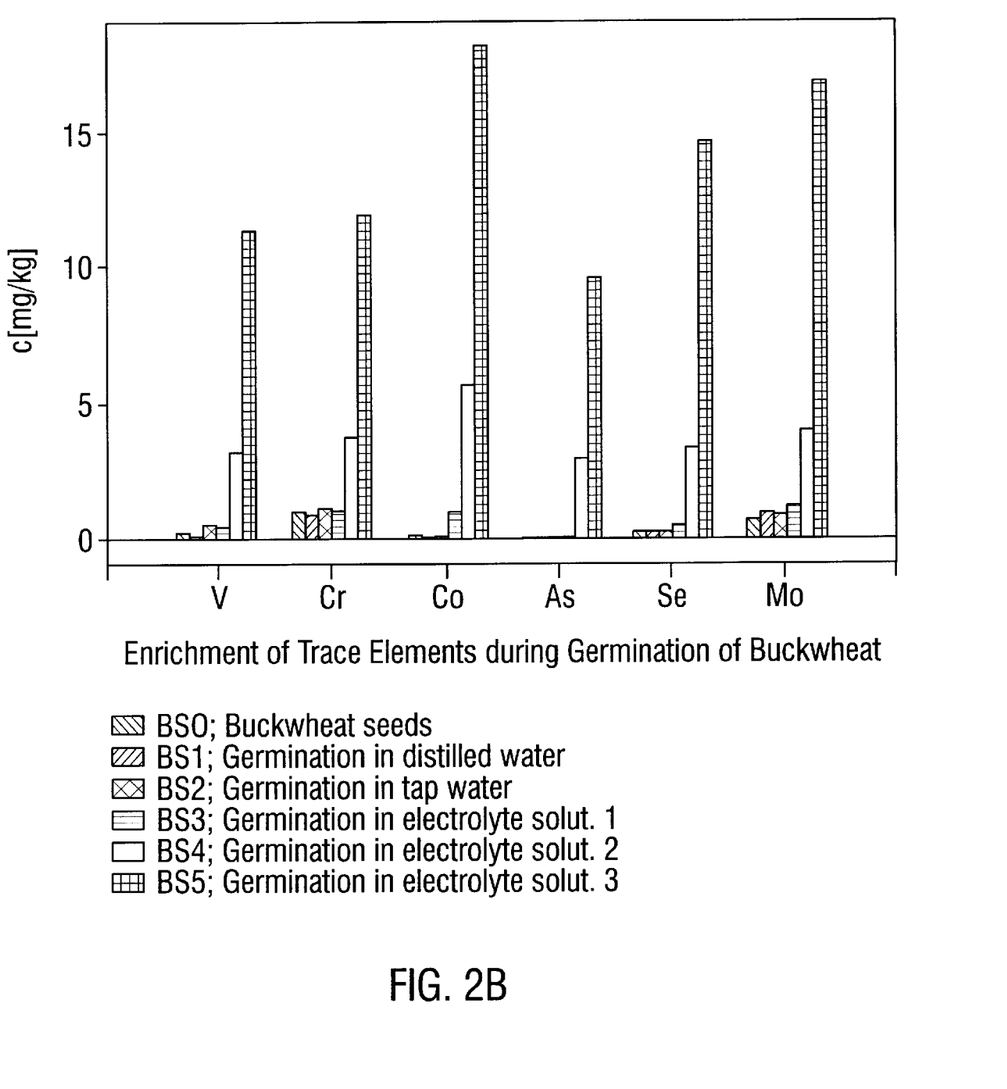
Figure 3A:
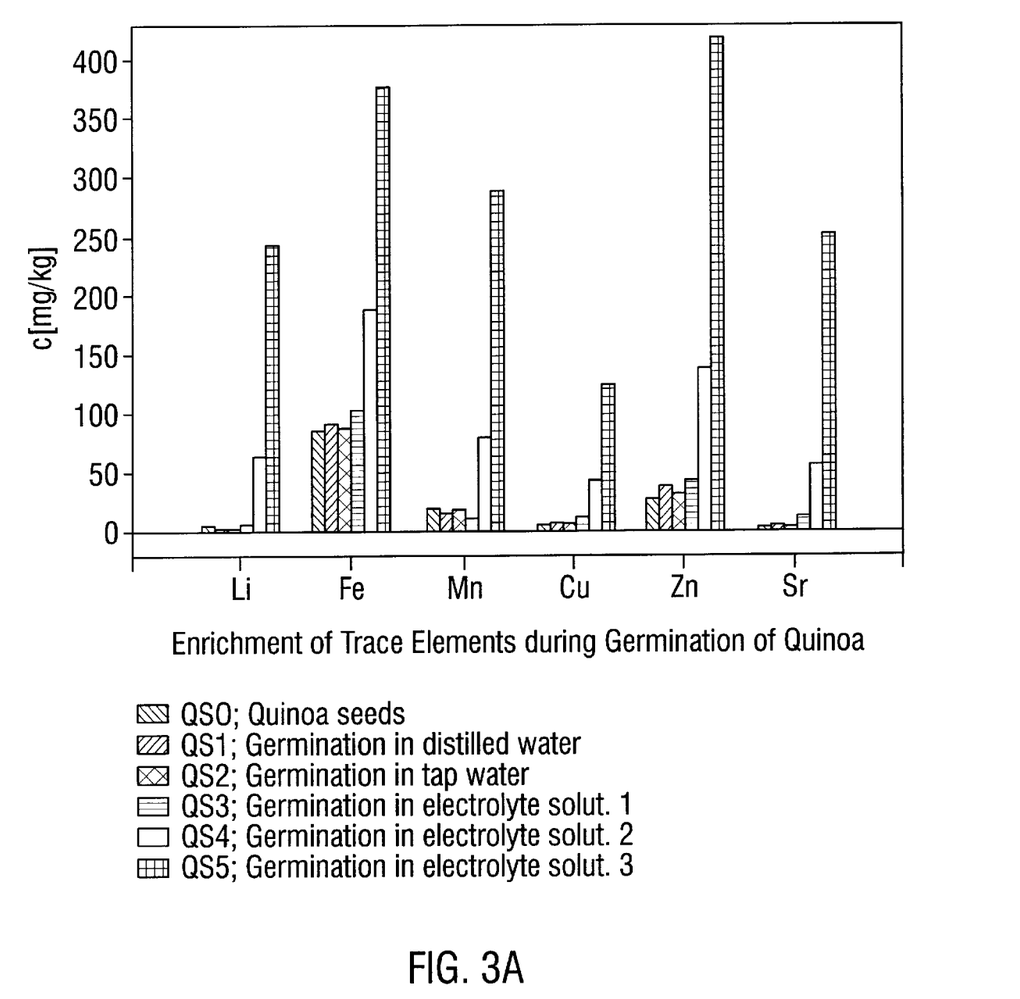
Figure 3B:
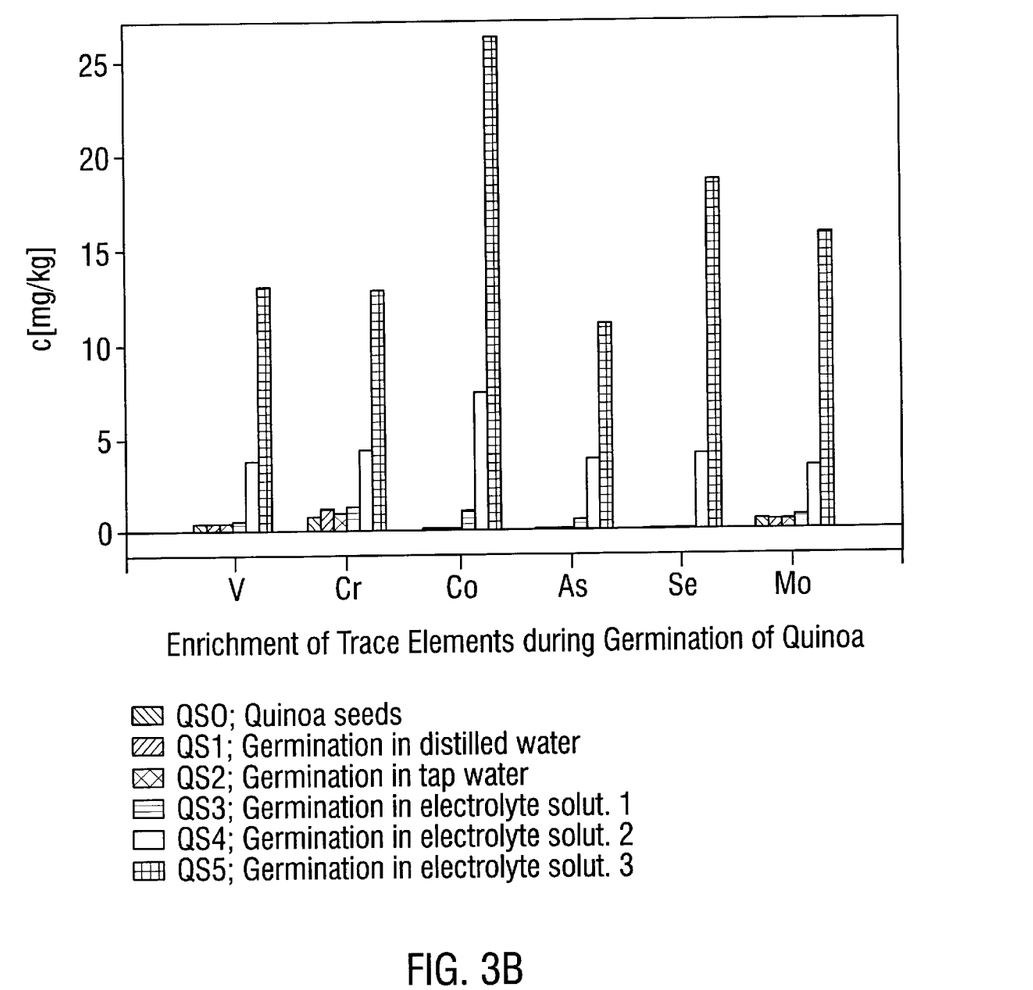

The results are summarized in Tables 5 and 6 along with FIGS. 1–3. From these it appears clearly that the germination of the seeds in an electrolyte solution leads to a marked increase in the electrolyte content of the plant embryos, while for many an ion species germination in distilled water or in tap water, respectively, resulted in a decline of the concentration of this ion species.

TABLE 5

Trace Element Concentrations in Wheat,
Buckwheat and Quinoa Seeds and Plant Embryos
Data in mg/kg dry weight

| | WS0 | WS1 | WS2 | WS3 | WS4 | WS5 |
|---|---|---|---|---|---|---|
| Li | 0.50 | <0.01 | <0.01 | 3.80 | 24.2 | 64.3 |
| V | 0.53 | 1.74? | 0.63 | 0.99 | 3.11 | 6.03 |
| Cr | 0.63 | 0.59 | 0.72 | 0.95 | 2.10 | 4.58 |
| Fe | 53.2 | 54.1 | 63.0 | 70.0 | 108 | 146 |
| Mn | 29.9 | 26.8 | 29.1 | 35.8 | 83.4 | 129 |
| Co | 0.06 | 0.01 | <0.01 | 0.96 | 4.80 | 9.82 |
| Ni | 0.05 | 0.16 | 0.14 | 0.23 | 0.50 | 0.64 |
| Cu | 4.68 | 4.80 | 4.76 | 7.88 | 23.9 | 44.4 |
| Zn | 28.6 | 33.9 | 29.5 | 41.2 | 95.2 | 155 |
| As | <0.3 | <0.3 | <0.3 | <0.3 | 1.1 | 4.5 |
| Se | <0.3 | <0.3 | <0.3 | <0.3 | 1.7 | 5.4 |
| Sr | 1.93 | 1.50 | 1.21 | 8.60 | 50.2 | 107 |
| Mo | 1.08 | 1.00 | 1.01 | 1.28 | 3.10 | 6.26 |
| Cd | 0.04 | 0.05 | 0.05 | 0.06 | 0.06 | 0.06 |
| Pb | 0.04 | 0.09 | 0.05 | 0.16 | 0.04 | 0.02 |

| | BS0 | BS1 | BS2 | BS3 | BS4 | BS5 |
|---|---|---|---|---|---|---|
| Li | 0.19 | 0.09 | 0.05 | 5.25 | 39.8 | 164 |
| V | 0.27 | 0.17 | 0.50 | 0.44 | 3.21 | 11.4 |
| Cr | 0.95 | 0.84 | 1.08 | 0.98 | 3.67 | 11.9 |
| Fe | 67.0 | 74.5 | 79.5 | 71.4 | 125 | 280 |
| Mn | 16.2 | 18.8 | 19.2 | 24.6 | 68.5 | 184 |
| Co | 0.07 | 0.09 | 0.09 | 0.76 | 5.56 | 18.2 |
| Ni | 3.14 | 4.18 | 3.56 | 3.25 | 3.58 | 3.99 |
| Cu | 7.29 | 9.18 | 8.60 | 9.73 | 26.2 | 71.3 |
| Zn | 25.8 | 38.6 | 32.6 | 38.2 | 98.7 | 247 |
| As | <0.3 | <0.3 | <0.3 | <0.3 | 3.0 | 9.6 |
| Se | 0.3 | 0.3 | 0.3 | 0.5 | 3.4 | 14.7 |
| Sr | 0.47 | 0.94 | 0.42 | 6.80 | 49.2 | 181 |
| Mo | 0.73 | 0.97 | 0.91 | 1.21 | 4.07 | 17.0 |
| Cd | 0.06 | 0.08 | 0.06 | 0.07 | 0.08 | 0.13 |
| Pb | <0.01 | 0.05 | 0.08 | 0.03 | 0.03 | 0.06 |

| | QS0 | QS1 | QS2 | QS3 | QS4 | QS5 |
|---|---|---|---|---|---|---|
| Li | 5.55 | 2.15 | 2.79 | 7.18 | 64.4 | 244 |
| V | 0.44 | 0.47 | 6.45 | 0.58 | 3.75 | 13.0 |
| Cr | 0.82 | 1.13 | 0.94 | 1.21 | 4.26 | 12.8 |
| Fe | 84.3 | 89.7 | 85.7 | 101 | 187 | 375 |
| Mn | 20.0 | 16.5 | 18.7 | 11.2 | 78.9 | 287 |
| Co | 0.05 | 0.06 | 0.05 | 0.97 | 7.30 | 26.2 |
| Ni | 0.12 | 0.10 | 0.08 | 0.09 | 0.52 | 1.52 |
| Cu | 5.88 | 7.68 | 7.31 | 11.9 | 42.4 | 123 |
| Zn | 27.1 | 37.3 | 31.6 | 42.0 | 138 | 419 |
| As | <0.3 | <0.3 | <0.3 | 0.4 | 3.7 | 10.8 |
| Se | <0.3 | <0.3 | <0.3 | <0.3 | 4 | 18.5 |
| Sr | 3.16 | 4.46 | 4.11 | 14.0 | 55.7 | 252 |
| Mo | 0.52 | 0.49 | 0.46 | 0.70 | 3.34 | 15.7 |
| Cd | 0.07 | 0.06 | 0.08 | 0.05 | 0.09 | 0.15 |
| Pb | 0.03 | 0.12 | 0.10 | 0.10 | 0.08 | 0.07 |

TABLE 6

Trace element concentration in seeds and in plant embryos after washing with hot water
Data in mg/kg dry weight

|    | WS5   | WS5H  | BS5   | BS5H  | QS5   | QS5H  |
|----|-------|-------|-------|-------|-------|-------|
| Li | 64.3  | 56.6  | 164   | 139   | 244   | 138   |
| V  | 6.03  | 5.27  | 11.4  | 16?   | 13.0  | 10.2  |
| Cr | 4.58  | 4.44  | 11.9  | 11.3  | 12.8  | 10.4  |
| Fe | 146   | 171   | 280   | 259   | 375   | 332   |
| Mn | 129   | 134   | 184   | 154   | 287   | 244   |
| Co | 9.82  | 9.83  | 18.2  | 12.7  | 26.2  | 20.3  |
| Ni | 0.64  | 0.77  | 3.99  | 3.22  | 1.52  | 1.27  |
| Cu | 44.4  | 44.3  | 71.3  | 61.7  | 123   | 102   |
| Zn | 155   | 165   | 247   | 203   | 419   | 372   |
| As | 4.5   | 3.3   | 9.6   | 8.2   | 10.8  | 9.3   |
| Se | 5.4   | 5.0   | 14.7  | 12.2  | 18.5  | 14.1  |
| Sr | 107   | 106   | 181   | 155   | 252   | 221   |
| Mo | 6.26  | 5.90  | 17.0  | 20.0  | 15.7  | 9.40  |
| Cd | 0.06  | 0.07  | 0.13  | 0.12  | 0.15  | 0.13  |
| Pb | 0.02  | 0.02  | 0.06  | 0.10  | 0.07  | 0.05  |

|    | WS1H  | WS2H  | WS3H  | WS4H  | BS1H  | BS2H  | BS3H  | BS4H  |
|----|-------|-------|-------|-------|-------|-------|-------|-------|
| Li | 0.18  | 0.06  | 2.64  | 18.50 | 0.57  | 0.28  | 5.16  | 35.20 |
| V  | 1.52  | 0.78  | 1.15  | 2.62  | 0.04  | 0.00  | 0.32  | 3.73  |
| Cr | 0.84  | 0.72  | 0.82  | 1.84  | 0.89  | 0.78  | 0.94  | 3.65  |
| Fe | 74.0  | 56.7  | 42.0  | 90.5  | 74.9  | 52.8  | 60.1  | 115.8 |
| Mn | 27.9  | 28.1  | 31.3  | 75.6  | 18.6  | 18.4  | 24.4  | 64.2  |
| Co | 0.01  | 0.00  | 0.66  | 4.20  | 0.09  | 0.06  | 0.74  | 4.40  |
| Ni | 0.09  | 0.05  | 0.17  | 0.34  | 3.96  | 2.75  | 2.98  | 2.84  |
| Cu | 4.87  | 4.31  | 6.31  | 21.00 | 9.23  | 7.40  | 9.89  | 24.93 |
| Zn | 35.2  | 28.2  | 35.0  | 85.5  | 38.1  | 29.4  | 38.9  | 92.7  |
| As | <0.3  | <0.3  | <0.3  | 0.8   | <0.3  | <0.3  | <0.3  | 2.50  |
| Se | <0.3  | <0.3  | <0.3  | 1.5   | 0.50  | 0.40  | 0.50  | 3.00  |
| Sr | 1.57  | 1.15  | 6.48  | 44.80 | 1.04  | 0.50  | 7.26  | 49.70 |
| Mo | 1.02  | 1.01  | 1.21  | 2.62  | 1.09  | 0.99  | 1.25  | 3.97  |
| Cd | 0.04  | 0.04  | 0.05  | 0.05  | 0.08  | 0.06  | 0.06  | 0.07  |
| Pb | 0.07  | 0.04  | 0.07  | 0.02  | 0.05  | 0.05  | 0.07  | 0.04  |

|    | QS1H  | QS2H  | QS3H  | QS4H  |
|----|-------|-------|-------|-------|
| Li | 2.34  | 2.89  | 5.47  | 39.23 |
| V  | 0.12  | 0.40  | 0.60  | 2.80  |
| Cr | 0.69  | 0.89  | 1.17  | 3.97  |
| Fe | 84.0  | 107.0 | 115.0 | 195.0 |
| Mn | 15.4  | 20.0  | 11.1  | 74.0  |
| Co | 0.05  | 0.05  | 0.89  | 6.59  |
| Ni | 0.47  | 0.67  | 0.59  | 0.76  |
| Cu | 6.97  | 7.43  | 12.00 | 44.45 |
| Zn | 35.2  | 33.2  | 41.1  | 137.0 |
| As | <0.3  | <0.3  | <0.3  | 3.10  |
| Se | <0.3  | <0.3  | <0.3  | 3.40  |
| Sr | 3.85  | 3.95  | 13.50 | 55.60 |
| Mo | 0.52  | 0.53  | 0.67  | 2.56  |
| Cd | 0.05  | 0.07  | 0.12  | 0.11  |
| Pb | 0.10  | 0.11  | 0.09  | 0.06  |

Determination of the Ascorbic Acid Concentration During Germination of Quinoa

For this test, quinoa seeds were germinated in distilled water (QS1, QS1H), tap water (QS2, QS2H) and electrolyte solutions 2 (QS4, QS4H) and 3 (QS5, QS5H), respectively.

2.1. Extraction

Approximately 0.8 g of sample were exactly weighed into a 12 ml centrifuge tube and admixed with 5 ml extraction solution (5% meta-phosphoric acid, 8% acetic acid and 0.005M EDTA). Subsequently, the tube was tightly sealed and intensively shaken for 4 minutes. After the extraction, the sample solution was centrifuged for 5 min at 10000 rpm. Prior to HPLC analysis, the clear supernatant solution was filtered through an 0.2 µm cellulose nitrate filter.

2.2. HPLC Analysis

The vitamin C concentration was determined by means of ion pair reversed phase HPLC and UV detection at 265 nm. The chromatographic parameters are summarized in Table 7. Quantitation was effected by means of an external calibration curve. A 1000 mg/l stock solution (100 mg vitamin C (Merck p.a.) in 100 ml extraction solution) was used as the standard solution. The standards for the calibration curve (20, 50 and 100 mg/l) were prepared by respective dilutions with the extraction solution.

TABLE 7

Chromatographic Parameters for Determining Vitamin C.

| Column: | Hamilton PRP1; 10 µm, 4 × 250 mm |
|---------|----------------------------------|
| Mobile phase: | 0.2M Na acetate; |
| | 5 mM tetrahexyl ammonium bromide |

TABLE 7-continued

Chromatographic Parameters for Determining
Vitamin C.

| | |
|---|---|
| | (THAB), pH 4.80 |
| Flow rate: | 1.5 ml/min (2000 psi) |
| Injection volume: | 100 μl |
| Detection: | UV 265 nm |

The results are shown in Table 8. Hence follows that the vitamin C concentration of the plant embryos increased in seeds germinated in electrolyte.

TABLE 8

Vitamin C Concentrations in Quinoa Seeds
and Plant Embryos

| Quinoa | c [mg/100 g] |
|---|---|
| QS0 | n.m. |
| QS1 | 6.0 |
| QS1H | 3.5 |
| QS2 | 7.4 |
| QS2H | 2.9 |
| QS4 | 7.9 |
| QS4H | 3.2 |
| QS5 | 6.7 |
| QS5H | 4.2 | n.m. = not measured

3. Determination of the thiamin concentration in mung bean, fenugreek and radish seeds were soaked in tap water (MS2, BoS2, RS2) and in an electrolyte solution 4 according to Table 9 (MS6, BoS6, RS6) for 10 to 12 hours. After soaking, germination took place at room temperature and normal day-night light ratios in commercial germinators comprised of transparent, superimposed plastics dishes with drainage means. The germination time was 3 days on an average; the plant embryos were thoroughly washed twice per day with tap water. After the germination, the samples were directly filled into plastic bags and deep-frozen.

Before drying, the samples of the plant embryos treated with electrolyte solution 4 were washed three times with tap water and subsequently three times with triple-distilled water. The plant embryos germinated in tap water were dried directly, without an additional treatment. Drying was effected according to item 1.2.

TABLE 9

Trace Element and Mineral Concentration of
the Electrolyte Solution (Electrolyte Solution 4) Used
for Germination for Thiamin Concentration. (When
dissolved in tap water, a precipitate forms).

| Substance | c[mg/l] | Element | c[mg/l] |
|---|---|---|---|
| Potassium hydrogen phosphate | 1605.6 | K | 720 |
| Magnesium phosphate 30% $H_2O$ | 708 | Mg | 100 |
| Zinc sulfate x $7H_2O$ | 22 | Zn | 5 |
| Ferrous gloconate | 44.7 | Fe | 5 |
| Manganese chloride | 29.5 | Mn | 10 |
| Copper gluconate | 71.4 | Cu | 10 |
| Sodium selenite | 0.33 | Se | 0.10 |
| Sodium molybdate | 0.25 | Mo | 0.10 |
| Chromic chloride | 0.51 | Cr | 0.10 |

TABLE 9-continued

Trace Element and Mineral Concentration of
the Electrolyte Solution (Electrolyte Solution 4) Used
for Germination for Thiamin Concentration. (When
dissolved in tap water, a precipitate forms).

| Substance | c[mg/l] | Element | c[mg/l] |
|---|---|---|---|
| Strontium lactate | 16.85 | Sr | 5 |
| Lithium carbonate | 26.75 | Li | 5 |

3.2. Analysis Procedure

Of all samples, two determinations each were carried out.

Hydrolysis and Enzymatic Splitting

Prior to hydrolysis, the dried samples were homogenized in an analyzing mill (Retsch). Subsequently, 0.50 g sample were exactly weighed into a 12 ml centrifuge tube (Pyrex). 8.5 ml 9.1M HCl were added to the sample; the tubes were tightly sealed and kept in a water-bath at 100° C. for 30 min and shaken several times. After cooling of the tubes, 0.5 ml 2.5M sodium acetate solution were added to the strongly acidic solution. Thereby, the pH was adjusted to a value of 4.5–4.6. Thereafter, 1 ml of the enzyme suspension (1 g diastasis, Merck 1.03604, in 10 ml $H_2O$+1 drop of antifoaming agent) were added, and the sample was shaken over night at room temperature.

Oxidation of the Thiamine into Thiochromium

Following the enzymatic splitting, the sample solution was centrifuged for 20 min at 3000 rpm. 1 ml of the supernatant solution was pipetted into a polystyrene tube. 0.5 ml oxidating agent (1 ml of a 1% $K_3[Fe(CN)_6]$ solution+ 10 ml 15% NaOH) was added to this solution and mixed thoroughly (drawing up 5 times with an 0.5 ml transfer pipette). Thereafter the oxidation reaction was stopped by neutralizing with 0.2 ml 40% phosphoric acid ($H_3PO_4$ 80%: $H_2O$ 1:1 v/v).

HPLC Analysis

Prior to the chromatographic separation, the oxidated sample solutions were centrifuged for 10 min at 10000 rpm. The clear solutions were used for the analysis without a further treatment. The chromatographic parameters are summarized in Table 10.

TABLE 10

Chromatographic Parameters for
Determining Thiamine

| | |
|---|---|
| Column: | Hamilton PRP1; 10 μm, 4 x 250 mm |
| Mobile phase: | $H_2O$:MeOH 60:40 v/v |
| Flow rate: | 1 ml/min (2500 psi) |
| Injection volume: | 100 μl |
| Detector: | Fluoreszenz 375/435 |

Preparation of the Standard Solution

As the stock solution, approximately 100 mg thiamine hydrochloride (Fluka 95160) were weighed exactly into a 50 ml volumetric flask. The latter was filled up to the 50 ml mark and thoroughly shaken. For quantitation by means of HPLC, this solutilon was diluted 1:10000 and subsequently oxidated with potassium hexacyanoferrate analogously to the sample solutions. To provide the calibration curve, the oxidated solution was diluted once more 1:1 and 1:3 with water.

3.3. Results

Figure 4A:
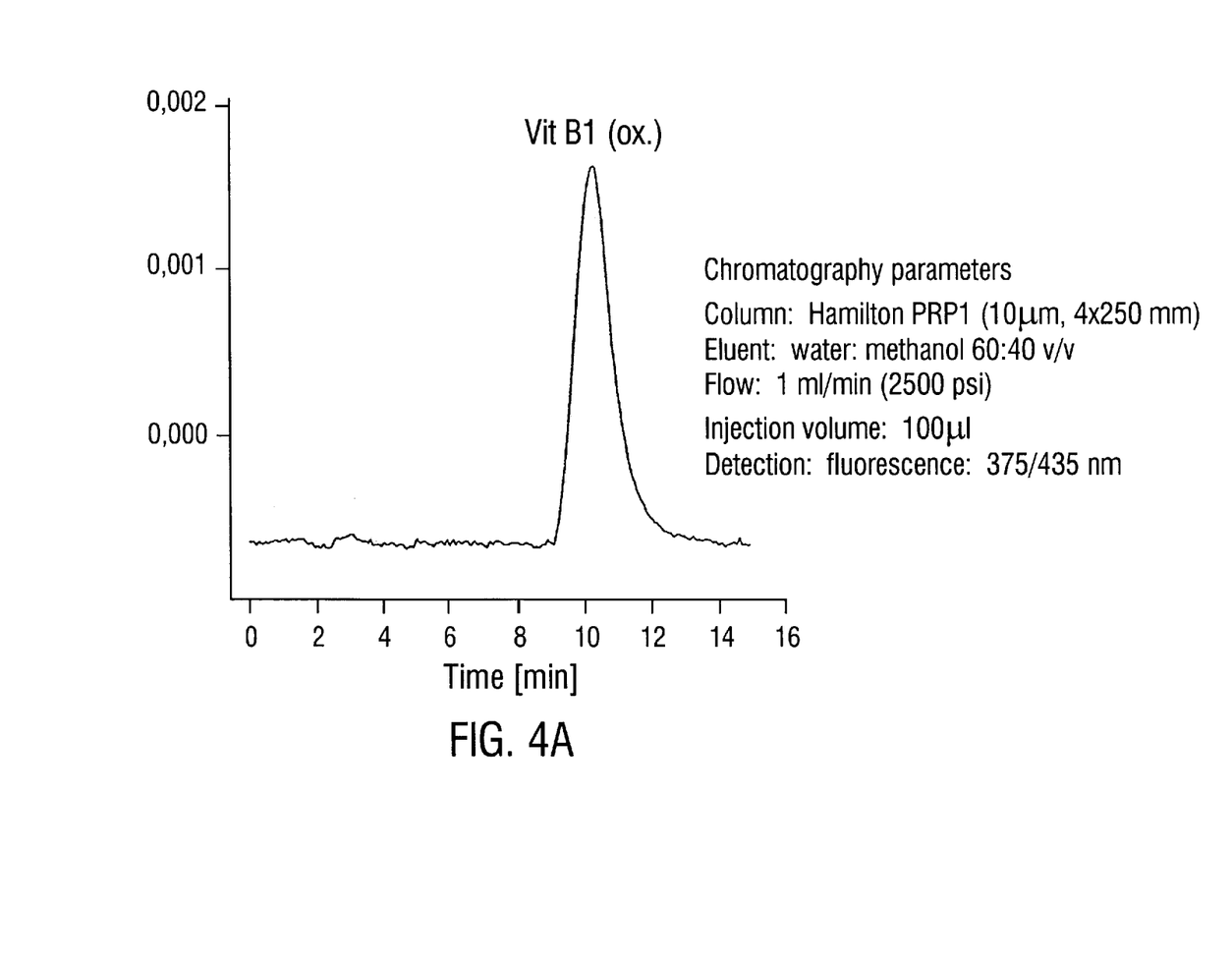
Figure 4B:
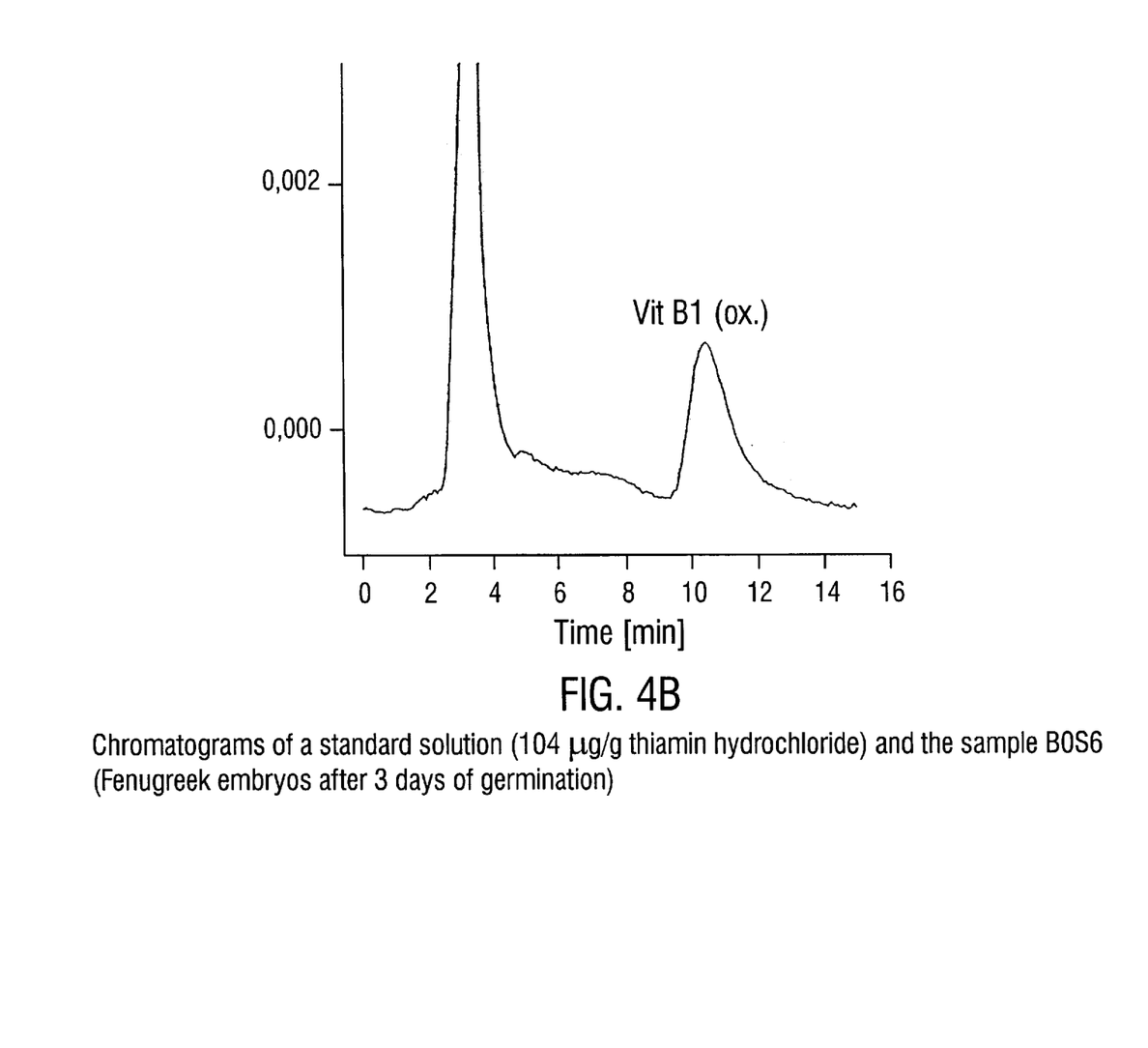

In FIG. 4 the chromatograms of a standard solution (104 μg/l) and of the sample BoS6 (fenugreek embryos) can be seen. The peak after 10 min corresponds to the thiochromium (oxidated and strongly fluorescent form of the thiamine). The thiamine concentrations of the individual samples are summarized in Table 11.

TABLE 11

Thiamine Concentrations (Based on Thiamine Hydrochloride) in Plant Embryos and Seeds; Concentration Data in mg/100 g.

| Mung Bean | | Fenugreek | | Radish | |
| --- | --- | --- | --- | --- | --- |
| Sample | Vit. $B_1$ | Sample | Vit. $B_1$ | Sample | Vit. $B_1$ |
| MSO | 0.03 | BoSO | <0.02 | RSO | n.d. |
| MS2 | 0.02 | BoS2 | 0.05 | RS2 | <0.02 |
| MS6 | 0.08 | BoS6 | 0.21 | RS6 | 0.02 |

During the germination of fenugreek, a marked increase in the thiamin concentration could be observed. In the seed, practically no vitamin $B_1$ could be detected (<0.02 mg/100 g), while up to 0.21 mg/100 g vitamin $B_1$ was present in the plant embryos. Likewise, the thiamin concentration in the mung bean sample increased during germination. What is striking is that the plant embryos of the electrolyte solution exhibit a much higher increase as compared to the plant embryos of the tap water.

The radish embryos contained only a very slight amount of thiamine. Therefore, it could not be determined whether or not the thiamine concentration for RS2 had decreased during germination thereof. However, an increase in the thiamine concentration in the sample RS6 could clearly be detected.

What is claimed is:

1. A method of producing electrolyte-enriched plant embryos comprising introducing germinative seeds comprising plant embryos into an electrolyte solution, and incubating said plant embryos in said electrolyte solution at a suitable temperature and for a period of time sufficient to attain an electrolyte enrichment within said plant embryos, wherein said electrolyte solution comprises:

at least one of zinc, iron, potassium, and magnesium ions;

at least one of copper, manganese, strontium and lithium ions; and at least one of selenium, molybdenum, chromium, arsenic, vanadium and cobalt ions.

2. A method as set forth in claim 1, wherein said plant embryos are selected from the group consisting of wheat, buckwheat, quinoa, mung bean, fenugreek; radish, alfalfa, maize, squash, rye, barley, rice, adzuki bean, pea, millet, chick pea, cress, linseed, lentil, mustard, sesamum, soybean, sunflower and amaranth embryos.

3. A method as set forth in claim 1, wherein said electrolyte solution comprises at least 1 mg/l of at least one of zinc, iron, potassium and magnesium ions, at least 0.5 mg/l of at least one of copper, manganese, strontium and lithium ions, at least 0.1 mg/l of at least one of selenium, molybdenum, chromium, arsenic, vanadium and cobalt ions.

4. A method as set forth in claim 1, wherein said electrolyte solution comprises at least 10 mg/l of at least one of zinc, iron, potassium and magnesium ions, at least 5 mg/l or at least one of copper, manganese, strontium and lithium ions, at least 1 mg/l of at least one of selenium, molybdenum, chromium, arsenic, vanadium and cobalt ions.

5. A method as set forth in claim 1, wherein said electrolyte solution comprises at least 50 mg/l of at least one of zinc, iron, potassium and magnesium ions, at least 25 mg/l or at least one of copper, manganese, strontium and lithium ions, at least 5 mg/l of at least one of selenium, molybdenum, chromium, arsenic, vanadium and cobalt ions.

6. A method as set forth in claim 1, wherein said suitable temperature for incubating said plant embryos ranges between 10° and 50° C.

7. A method as set forth in claim 1, wherein said suitable temperature for incubating said plant embryos ranges between 20° and 30° C.

8. A method as set forth in claim 1, wherein said period of time for incubating said plant embryos ranges from approximately 12 to 240 hours.

9. A method as set forth in claim 1, wherein said period of time for incubating said plant embryos ranges from approximately 60 to 100 hours.

10. A method as set forth in claim 1, further comprising washing and drying said incubated plant embryos.

11. A method as set forth in claim 10, further comprising processing said washed and dried plant embryos in a manner suitable for sales purposes.

12. A method as set forth in claim 1, wherein said electrolyte solution comprises at least 0.5 mg/l copper ions, 1 mg/l zinc ions, 0.1 mg/l cobalt ions.

13. A method as set forth in claim 12, wherein said electrolyte solution further comprises at least 0.1 mg/l molybdenum ions, 0.5 mg/l lithium ions, 1 mg/l selenium ions and 1 mg/l vanadium ions.

* * * * *